United States Patent
Dyke et al.

(10) Patent No.: US 7,015,234 B2
(45) Date of Patent: Mar. 21, 2006

(54) HYDROXAMIC ACID DERIVATIVES

(75) Inventors: Hazel Joan Dyke, Hempstead (GB); Robert John Watson, Cambridge (GB)

(73) Assignee: Celltech R & D Limited, Berkshire (GB)

(*) Notice: Subject to any disclaimer, the term of this patent is extended or adjusted under 35 U.S.C. 154(b) by 225 days.

(21) Appl. No.: 10/485,905

(22) PCT Filed: Aug. 7, 2002

(86) PCT No.: PCT/GB02/03656

§ 371 (c)(1),
(2), (4) Date: May 25, 2004

(87) PCT Pub. No.: WO03/014101

PCT Pub. Date: Feb. 20, 2003

(65) Prior Publication Data

US 2004/0192733 A1 Sep. 30, 2004

(30) Foreign Application Priority Data

Aug. 9, 2001 (GB) .............................. 0119396

(51) Int. Cl.
*A01N 43/40* (2006.01)
*A61K 31/445* (2006.01)

(52) U.S. Cl. ...................... 514/327; 546/207
(58) Field of Classification Search ................ 546/207; 514/327
See application file for complete search history.

(56) References Cited

U.S. PATENT DOCUMENTS

| 4,166,452 A | 9/1979 | Generales, Jr. ............. 128/741 |
| 4,256,108 A | 3/1981 | Theeuwes ................... 128/260 |
| 4,265,874 A | 5/1981 | Bonsen et al. ................ 424/15 |
| 6,187,924 B1 * | 2/2001 | Baxter et al. ............... 544/374 |

FOREIGN PATENT DOCUMENTS

| WO | WO 99/24399 | * | 5/1999 |
| WO | WO 00/46221 |   | 8/2000 |
| WO | WO 00/462221 | * | 8/2000 |

OTHER PUBLICATIONS

Copy of the PCT International Search Report dated Oct. 24, 2002 (PCT/GB02/03656.
Barta, T.E., et al., "Synthesis and activity of selective MMP inhibitors with an aryl backbone," *Bioorganic & Medicinal Chem. Letts.*, 2000, 10, 2815–2817.
Barta, T.E., "Selective, orally active MMP inhibitors with an aryl backbone," *Bioorganic & Medicinal Chem. Letts.*, 2001, 11, 2481–2483.
Hooper, N.M., et al., "Review Article: membrane protein secretases," *Biochem. J.*, 1997, 321, 265–279.
Solorzano, C.C., et al., "Involvement of 26–kDa cell–associated TNF–α in experimental hepatitis and exacerbation of liver injury with a matrix metalloproteinase inhibitor," *J. of Immunol.*, 1997, 158, 414–419.

* cited by examiner

*Primary Examiner*—Johann Richter
*Assistant Examiner*—Chukwuma Nwaonicha
(74) *Attorney, Agent, or Firm*—Woodcock Washburn LLP

(57) ABSTRACT

Compounds of the general formula (I)

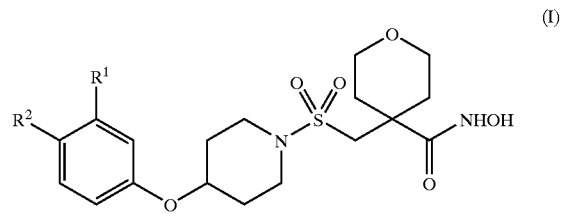

are described wherein $R^1$ and $R^2$, which may be the same or different, is each a hydrogen atom or a $CF_3$, $CF_2H$ or $CFH_2$ group, provided that when one of $R^1$ and $R^2$ is a hydrogen atom, then the other is a $CF_3$, $CF_2H$ or $CFH_2$ group, and the salts, solvates or hydrates thereof. Compounds of the invention are potent MMP inhibitors which advantageously do not cause tendonitis in a relevant animal model. Compounds of the invention may be expected to be of use in medicine, especially where the avoidance of side effects, such as joint pain, is desired.

8 Claims, No Drawings

HYDROXAMIC ACID DERIVATIVES

FIELD OF INVENTION

This invention relates to hydroxamic acid derivatives and their use in medicine.

BACKGROUND OF THE INVENTION

Matrix metalloproteinases (MMPs) are a group of structurally related endopeptidases that degrade the proteinaceous elements of the extracellular matrix. A number of important features are shared by members of the MMP family and these include a zinc atom at the catalytic site, catalytic activity at neutral pH, initial existence as inactive proenzymes, activation involving renewal of an N-terminal domain, structural stabilisation by calcium, and inhibition of the catalytically active forms by a family of specific protein inhibitors called Tissue Inhibitors of Metalloproteinases (TIMPs). The classical MMP family currently consists of at least twenty members including the collagenases, gelatinases, stromelysins and membrane-type MMPs.

The MMPs are a sub-family of a much larger group of zinc-containing proteinases which include the Reprolysins and Serralysins, and the Astacin family.

It has been demonstrated that some compounds which inhibit the classical MMPs also have the capability to inhibit a number of other events that are mediated by non-matrix metalloproteinases (MPs) which includes the release of TNFα, CSF-1 and TGFα, and the shedding of L-selectin and the IL-6, TNF-R1, and TNF-RII receptors. See Hooper et al (1997), Biochem. J., 321: 265–279.

Matrix metalloproteinases have been associated with many disease conditions. Inhibition of the activity of one or more of the MMPs could therefore be of benefit in these disease conditions. Such conditions include cancer, inflammation, autoimmune, infectious or ocular disease. See Whittaker M. et al, (1999) Chem. Rev., 99, 2735–2776 and (1994) Annals of the New York Academy of Sciences, Vol 732.

Thus compounds with MMP inhibitory properties may be used for treating a number of different diseases. Of particular benefit are those compounds which also have good pharmacokinetic properties.

However, the inhibition of non-matrix metalloproteinases (MPs) by these compounds may offer no therapeutic benefit and indeed could be deleterious. For example, it has been suggested that MMP inhibitors which also inhibit the release of TNFα may have a role in exacerbating liver injury; see Solorzano at al (1997), J. Immounol., 158:414–419.

Similarly, early clinical evidence from the use of MMP inhibitors, which are not selective for the classical MMPs alone, suggests that their use is associated, in many patients, with joint pain (tendonitis). See Wojtowicz-Praga et al, Lombardi Cancer Center, Georgetown University Hospital DC & BBL Anapolis Md. Am. Soc. Clin. Oncol. (May 1996) "The Pharmacokinetics (PK) of Marimastat (BB-2516), A Novel Metalloproteinase Inhibitor (MMPI) administered orally to patients with metastatic lung cancer". The development of joint pain is dose-limiting and may require treatment "holidays", for up to 50% of the course of treatment, or the administration of non-steroidal anti-inflammatory agents (NSAIDs).

There is therefore a need for selective MMP inhibitors which can be used in medicine at dosages at which they do not cause undesired side-effects, such as joint pain.

WO 99/24399 discloses a class of hydroxamic acid derivatives as MMP inhibitors.

SUMMARY OF THE INVENTION

We have now found a number of compounds which are potent MMP inhibitors which advantageously do not cause tendonitis in a relevant animal model. The compounds may be expected to be of use in medicine, especially where the avoidance of side effects such as joint pain is desired. Therefore the compounds of the invention may be expected to have a superior side-effect profile compared to compounds, such as Marimastat®, which is known to be associated with dose limiting effects.

Thus we provide a compound of formula (1)

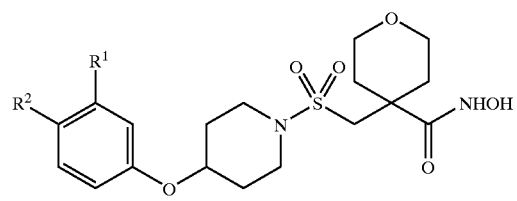

(I)

wherein:

$R^1$ and $R^2$, which may be the same or different, is each a hydrogen atom or a $CF_3$, $CF_2H$ or $CFH_2$ group, provided that when one of $R^1$ or $R^2$ is a hydrogen atom the other is a $CF_3$, $CF_2H$ or $CFH_2$ group;

and the salts, solvates or hydrates thereof.

DESCRIPTION OF THE INVENTION

In one particular group of compounds of the invention $R^1$ a hydrogen atom and $R^2$ is a $CF_3$, $CF_2H$ or $CFH_2$ group. In another particular group of compounds of the invention $R^2$ a hydrogen atom and $R^1$ is a $CF_3$, $CF_2H$ or $CFH_2$ group.

Particularly preferred compounds of the invention are those described in the Examples.

An especially preferred compound of the invention is the compound of Formula 1, where $R^2$ is a $CF_3$ group and $R^1$ is a hydrogen atom, namely:

4-[4-(4-trifluoromethylphenoxy)piperidine-1-sulfonylmethyl]tetrahydropyran-4-carboxylic acid hydroxyamide.

It will be appreciated that where desired the compounds of the invention may be administered in a pro-drug form, for example, as the protected hydroxamic acid derivative, which may be protected as either N or O-substituted derivatives, such as O-benzyl or O-tert-butyl. It will be further appreciated that the pro-drugs may be converted in vivo to the active compounds of formula (I), and the invention is intended to extend to such pro-drugs.

Salts of the compounds of formula (I) include pharmaceutically-acceptable salts, for example base addition salts derived from inorganic or organic bases, for example alkali metal salts such as magnesium or calcium salts, and organic amine salts such as morpholine, piperidine, dimethylamine or diethylamine salts.

Compounds of the general formula (I) may be prepared by any suitable method known in the art and/or by the following processes. In the description and formulae below the groups $R^1$ and $R^2$ are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction sequence. Suitable protecting groups for such functionality will be apparent to those skilled in the art. For specific details see Greene T. W. et al "Protective Groups in Organic Synthesis" (1999).

Thus, for example, compounds of the invention may be prepared by the following general route as shown in scheme 1:

a tert-butoxycarbonyl ester group, this may be removed under acidic conditions, such as trifluoroacetic acid in a halogenated solvent e.g. dichloromethane.

The compound of formula (vi) may be prepared by reaction of a compound of a formula (iv) with a compound of formula (v) preferably in the presence of a base such as triethylamine in a halogenated solvent e.g. dichloromethane. It will be appreciated that the compound of formula (v) may be prepared in a similar manner to methods described in the literature.

The compound of formula (vi) may then be converted to a carboxylic acid using, for example, a base such as lithium

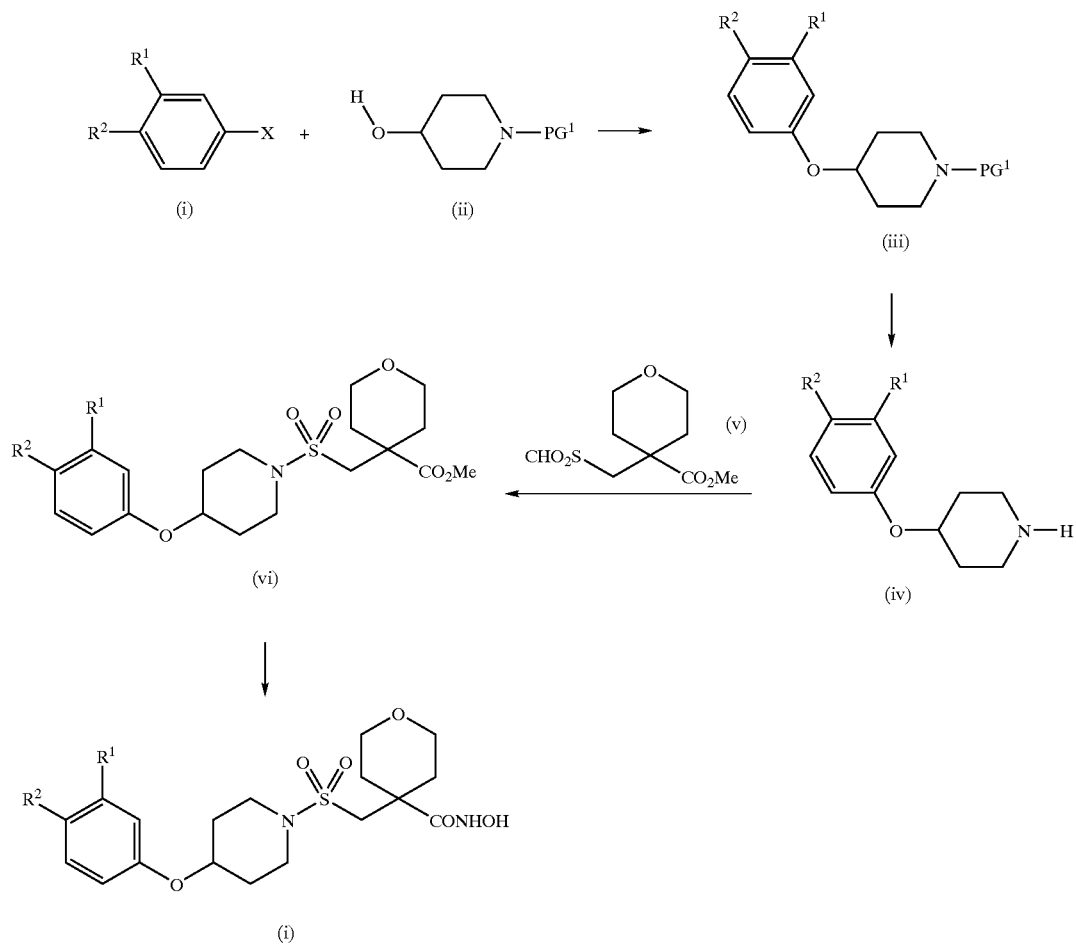

Scheme 1

Compounds of formula (iii) may be prepared by reacting a compound of formula (i) (where X is, for example, a hydroxy group or a leaving group, e.g. a fluorine atom) with a compound of formula (ii) (where $PG^1$ is a suitable protecting group, e.g. tert-butoxycarbonyl ester) using standard ether bond forming methodology. For example when X, in a compound of formula (i), is a fluorine atom such a compound of formula (i) may be reacted with a compound of formula (ii) in the presence of a suitable base, such as potassium tert-butoxide in an appropriate solvent, such as N,N-dimethylformamide (DMF), to yield a compound of formula (iii).

The protecting group, $PG^1$, may be removed using standard methods known to those skilled in the art, to give a compound of formula (iv). Thus for example, when $PG^1$ is hydroxide in a suitable solvent system, such as methanol and water at a suitable temperature, e.g. reflux temperature. The carboxylic acid thus formed may then be converted to a compound of formula (I) using conditions well known in the literature. For example, treatment of the acid with oxalyl chloride in an inert solvent (such as dichloromethane) in the presence of a catalytic amount of DMF gives an intermediate acid chloride, which may or may not be isolated, but which in turn is reacted with hydroxylamine at a suitable temperature such as room temperature to give the desired hydroxamic acids (I).

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The ability of the compounds to inhibit MMPs may be determined by use of an appropriate enzyme inhibition test, for example, as described in Example A.

Advantageously in our tests with compounds of the invention tendonitis has not been observed. A rat model, described in Example B, may be used to predict the propensity of the compounds of the invention to cause joint pain.

Advantageously the compounds of the invention have useful pharmacokinetic properties, for example, good bioavailability. The pharmacokinetic profile of the compounds may be determined using the assay method described in Example C.

This invention also relates to a method of treatment for patients (including man and/or mammalian animals raised in the dairy, meat or fur industries or as pets) suffering from disorders or diseases which can be attributed to MMPs as previously described, and more specifically, a method of treatment involving the administration of a matrix metalloproteinase inhibitor of formula (I) as the active constituent.

Accordingly, compounds of formula (I) can be used among other things in the treatment of osteoarthritis and rheumatoid arthritis, and in diseases and indications resulting from the over-expression of these matrix metalloproteinases such as found in certain metastatic tumour cell lines, or conditions involving ocular neovascularisation.

As mentioned above, a compound of formula (I) is useful in human or veterinary medicine since they are inhibitors of MMPs. Accordingly in another aspect, this invention concerns:

a method of management (by which is meant treatment or prophylaxis) of disease or conditions mediated by MMPs in mammals, in particular in humans, which method comprises administering to the mammal an effective amount of a compound of formula (I) above, or a pharmaceutically acceptable salt thereof; and a compound of formula (I) for use in human or veterinary medicine, particularly in the management (by which is meant treatment or prophylaxis) of diseases or conditions mediated by MMPs; and the use of a compound of formula (I) in the preparation of an agent for the management (by which is meant treatment or prophylaxis) of diseases or conditions mediated by MMPs.

The diseases or conditions referred to above include inflammatory diseases, autoimmune diseases, cancer, cardiovascular diseases, diseases involving tissue breakdown. Appropriate diseases include rheumatoid arthritis, osteoarthritis, osteoporosis, neurodegeneration, Alzheimer's disease, stroke, vasculitis, Crohn's disease, ulcerative colitis, multiple sclerosis, periodontitis, gingivitis, those involving tissue breakdown (such as bone resorption, haemorrhage, coagulation, acute phase response, cachexia and anorexia), acute infections, HIV infections, fever, shock states, graft versus host reactions, dermatological conditions, surgical wound healing, psoriasis, atopic dermatitis, epidermolysis bullosa, tumour growth, angiogenesis and invasion by secondary metastases, ophthalmological disease, retinopathy, corneal ulceration, reperfusion injury, migraine, meningitis, asthma, rhinitis, allergic conjunctivitis, eczema, anaphylaxis, restenosis, congestive heart failure, endometriosis, atherosclerosis, endosclerosis, aspirin-independent anti-thrombosis, systemic lupus erythematosus, solid organ transplant and ocular disorders.

The compounds of formula (I) may also be useful in the treatment of pelvic inflammatory disease (PID) and cancer-induced bone resorption. Further, they can be used in the treatment of lung diseases, e.g. selected from cystic fibrosis, adult respiratory distress syndrome (ARDS), emphysema, bronchitis obliterans-organising pneumonia (BOOP), idiopathic pulmonary fibrosis (PEF), diffuse alveolar damage, pulmonary Langerhan's cell granulamatosis, pulmonary lymphangioleiomyomatosis (LAM) and chronic obstructive pulmonary disease (COPD).

The compounds of the invention are particularly of use in the treatment of inflammatory diseases, autoimmune diseases, cancer and ocular disorders. Thus, for example, the compounds may be used in the treatment and/or prophylaxis of graft versus host reactions, psoriasis, atopic dermatitis, rhinitis, eczema, systemic lupus erythematosus, solid organ transplant, cystic fibrosis and especially rheumatoid arthritis, osteoarthritis, osteoporosis, Crohn's Disease, ulcerative colitis, multiple sclerosis, periodontitis, bone resorption, bacterial infections, epidermolysis bullosa, tumour growth, angiogenesis, ophthalmological disease, retinopathy, asthma, emphysema, bronchitis, and chronic obstructive pulmonary disease (COPD).

The diseases or conditions involving ocular neovascularization, include, but are not limited to, diabetic retinopathy, retinopathy of prematurity (ROP) or age-related macular degeneration (ARMD).

For the treatment of all diseases previously indicated, the compounds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injection, intravenous, intramuscular, intrasternal injection or infusion techniques. Ocular injection, such as intravitreal, subtenons, subconjunctival, periocular and retrobulbar may also be used, as well as intraocular slow release devices and implants. In addition to the treatment of warm-blooded animals such as mice, rats, horses, cattle, sheep, dogs, cats etc, the compounds of the invention are effective in the treatment of humans.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874, to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate polyvinyl-pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing a compound of formula (I) are employed. For topical ocular administration pharmaceutically acceptable solutions, suspensions or gels containing a compound of formula (I) may be used. Solutions and suspensions may also be adapted for intra-vitreal or intra-cameral use.

Dosage levels of the order of from about 0.05 mg to about 140 mg per kilogram of body weight per day are useful in the treatment of the above-indicated conditions (about 2.5 mg to about 7 g per patient per day).

The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

Salts of compounds of formula (I) may be prepared by reaction of a compound of formula (I) with an appropriate acid in a suitable solvent or mixture of solvents e.g. an organic solvent such as an ether e.g. diethylether, or an alcohol, e.g. ethanol using conventional procedures.

Chromatography, recrystallisation and other conventional separation procedures may also be used with intermediates or final products where it is desired to obtain a particular geometric isomer of the invention.

The following Examples illustrate the preparation of compounds of the invention. All temperatures are in ° C. The following abbreviations are used:

NMP—1-methyl-2-pyrrolidinone; DCM—dichloromethane;
TNF$\alpha$=Tumour Necrosis Factor$\alpha$; LPS=Lipopolysaccharide;
ELISA =Enzyme linked immunosorbant assay;
PBMC =Peripheral blood mononuclear cells;

PMA =Phorbol 12-myristate 13-acetate;
h=hour

All NMR's were obtained either at 300 MHz or 400 MHz.

All Intermediates and Examples were named with the aid of Beilstein Autonom (available from MDL Information Systems GmbH, Therdor-Heuss-Allee 108D 60486, Frankfurt, Germany) or were given names that seemed consistent.

EXAMPLE A

MMP Inhibition Activity-Fluorimetric Assay

The potency of a compound of formula (I) to act as an inhibitor of gelatinase-A (MMP-2) and gelatinase-B (MMP-9) was determined using the following procedure:

An inhibitor is dissolved in dimethylsulphoxide containing 0.02% β-mercaptoethanol and serial dilutions are prepared. Activated enzyme is incubated in assay buffer containing 50 mM Tris, pH 7.4, 5 mM $CaCl_2$, 0.002% $NaN_3$ and Brij 35 in the presence and absence of inhibitor. Samples are preincubated at 37° C. for 15 minutes before the addition of the fluorimetric substrate (Mca-Pro-Leu-Gly-Leu-Dpa-Ala-Arg-$NH_2$) to a final concentration of 10 μM. The assay is incubated for 20–30 min at 37° C. and then read in a Fluoroscan II at $\lambda_{ex}$(340 nm) and $\lambda_{em}$ (405 nm).

The enzyme activity was compared to activity in a control devoid of inhibitor and the results reported as that inhibitor concentration effecting 50% inhibition of the enzyme ($IC_{50}$).

EXAMPLE B

Rat Tendonitis Model

Tendonitis may be determined using the model as described in WO-A-9925693.

EXAMPLE C

Determination of Pharmacokinetic Profile

The pharmacokinetic profile of a compound of the invention is determined in rats cannulated in the right carotid artery for blood collection. For iv dosing, the compound is prepared in a suitable formulation, for example 10% v/v DMSO, 50% v/v PEG 400 in water, and dosing is carried out by cannulation of the left jugular vein. Samples are collected at 5 min, 0.5, 1,2, 4, 6 and 8 hours post-dosing. For oral dosing, a compound is prepared in a suitable formulation such as 0.4% w/v methylcellulose in water. Samples are collected at 0.5, 1,2, 4, 6 and 8 hours post-dosing. In some cases, samples are also collected at 12 hours post-dosing. Plasma is obtained by centrifugation of the blood sample and drug concentration is then determined using standard methods, such as liquid chromatography-mass spectrometry following protein precipitation.

Intermediate 1

4-(4-Trifluoromethylphenoxy)piperidine-1-carboxylic Acid Tert-butyl Ester

A stirred solution of 4-hydroxypiperidine-1-carboxylic acid tert-butyl ester (134.8 g) in N,N-dimethylformamide (850 m) was cooled in an ice bath under a nitrogen atmosphere. Potassium tert butoxide (75.2 g) was added in portions such that the temperature did not exceed 22° C. and the resulting mixture was maintained at 0° C. for a further 1.5 hours when 4-fluorobenzotrifluoride (100 g) was added dropwise over 15 minutes. The reaction mixture was allowed to warm to room temperature and stirred overnight. Water (200 ml) was added and the mixture was extracted with tert butyl methyl ether (1×400 ml, 1×300 ml, 1×200 ml). The combined organic extracts were washed with water (2×400 ml), brine (200 ml) and then dried over magnesium sulphate and evaporated in vacuo to leave the title compound as an off-white/pale yellow solid (206.4 g)

Mass spectrum m/z 331 $(M-14)^{30}$

Similarly prepared was

Intermediate 2

4-(3-Trifluoromethylphenoxy)piperidine-1-carboxylic Acid Tert-butyl Ester

Sodium hydride (0.9 g, 60% dispersion in mineral oil) was added to a solution of 4-hydroxypiperidine-1-carboxylic acid tert-butyl ester (4 g) in NMP (40 ml) and the solution stirred for 1 h, then a solution of 3-fluorobenzotrifluoride (3.5 g) in NMP (10 ml) was added and the mixture was stirred for 2 h at 80 ° C. The mixture was added to water (200 ml) and extracted with diethyl ether (2×100 ml), the solvent washed with water, 1 M sodium hydroxide and brine, dried and evaporated to give the title compound as yellow oil (5.2 g) which was carried through to the next step without purification.

Mass spectrum m/z 331 $(M-14)^+$

Intermediate 3

4-(4-Trifluoromethylphenoxy)piperidine

A stirred solution of Intermediate 1 (206 g) in dichloromethane (1236 ml) was cooled in an ice bath and trifluoroacetic acid (365 ml) added over 0.5 hour. Stirring was continued for a further 4.5 hours when the mixture was cooled in an ice bath and quenched with 4M sodium hydroxide solution until a pH $\geq 13$ was obtained. The layers were separated and the aqueous phase re-extracted with fresh dichloromethane (125 ml). The combined organic extracts were washed with brine (1×500 ml, 1×250 ml), dried over magnesium sulphate and then evaporated in vacuo. The title compound was obtained as an off white solid (101 g).

Mass spectrum m/z 246 $(M+1)^+$

Similarly prepared was

Intermediate 4

4-(3-Trifluoromethylphenoxy)piperidine

Prepared from intermediate 2 (5.2 g) following the procedure for intermediate 3 to give the title compound as off-white solid 4.2 g).

TLC $R_f$0.3 (1%$NH=_4OH$ in ethyl acetate)

Intermediate 5

4-[4-(4-Trifluoromethylphenoxy)piperidine-1-sulfonyl methyl]tetrahydropyran-4-carboxylic Acid Methyl Ester Triethylamine (12 ml) was added to a stirred solution of Intermediate 3 (9.6 g) in dichloromethane (50 ml) and the resulting mixture was cooled in an ice bath under a nitrogen atmosphere. A solution of methyl 4-(chlorosulfonyl) methyltetrahydropyran-4-carboxylate (CAS No. 374822-74-9) (10 g) in dichloromethane (50 ml) was then added dropwise over ca. 5 minutes and the resulting mixture was allowed to warm to room temperature and stirred overnight. Water (50 ml) was added and the layers separated. The aqueous layer was extracted with fresh DCM (30 ml) and the combined organic extracts were washed with water (40 ml), dilute hydrochloric acid (3×40 ml) and finally water (40 ml). The organic solution was transferred to a flask set for distillation at atmospheric pressure and concentrated to a volume of 50 ml. Tert. butyl methyl ether was added in portions (1×50 ml, 1×30 ml) and the mixture concentrated back to 50 ml after each addition. The mixture was stirred overnight at room temperature, cooled in an ice bath and the product recovered by filtration. The cake was washed with cold tert. butyl methyl ether (20 ml) and then dried in a vacuum oven to give the title compound as an off-white solid (12.5 g)

Mass spectrum m/z 466 (M+1)$^+$

Intermediate 6

4-[4-(4-Trifluoromethylphenoxy)piperidine-1-sulfonyl methyl]tetrahydropyran-4-carboxylic acid A mixture of Intermediate 5 (5 g) and lithium hydroxide monohydrate (0.9 g) in methanol (25 ml) and water (25 ml) was heated to reflux for 4.5 hours. The reaction was set for distillation at atmospheric pressure and water (33.5 ml) added in a 'put-and-take' fashion. Distillation was continued until the head temperature was >90° C. The resulting solution was cooled to 60–70° C. when concentrated hydrochloric acid (1.8 ml) was added dropwise. The mixture was allowed to cool to room temperature and stirred out overnight. The product was recovered by filtration, washed with water (4×10 ml) and dried in a vacuum oven to give the title compound as an off-white solid (4.42 g).

Mass spectrum m/z 450 (M−1)$^-$

Intermediate 8

4-[4-(3-Trifluoromethylphenoxy)piperidine-1-sulfonyl methyl]tetrahydropyran-4-carboxylic Acid Intermediate 4 (0.50 g) was added to a solution of methyl 4-(chlorosulfonyl) methyltetrahydropyran-4-carboxylate (0.60 g) in DCM and triethylamine (0.5 ml) was added. The solution was stirred for 2 h, then washed with aqueous citric acid (10% aq, 20 ml), water and brine, dried and evaporated. The residue was dissolved in methanol (20 ml) and a solution of lithium hydroxide (250 mg) in water (20 ml) was added. The solution was stirred at reflux for 2 h, cooled and evaporated to half volume. The aqueous solution was washed with diethyl ether, acidified with citric acid to pH 4 and extracted with DCM. The solvent was washed with water and brine, dried and evaporated to give the title compound as white solid (0.65 g). TLC R$_f$0.42 (diethyl ether)

Example 1

4-[4-(4-Trifluoromethylphenoxy)piperidine-1-sulfonyl methyl]tetrahydropyran-4-carboxylic Acid Hydroxyamide Oxalyl chloride (0.65 ml) was added dropwise to a stirred solution of Intermediate 6 (2.25 g) and N,N-dimethylformamide (39 μl) in tetrahydrofuran (35 ml). The resulting mixture was stirred at room temperature, under a nitrogen atmosphere, for ca.3 hours when the solvent was removed in vacuo. Toluene (1×20 ml, 1×10 ml) was added to the residue which was then re-evaporated after each addition of solvent. Tetrahydrofuran (27 ml) was added to the residue and the resulting solution cooled in an ice bath when hydroxylamine (1.5 ml of a 50% w/w solution in water) was added. The mixture was allowed to warm to room temperature and stirred for 2.5 hours. The reaction mixture was then distilled at atmospheric pressure and water (23.5 ml) added in a 'put-and-take' fashion until a head temperature of >65° C. was achieved. The mixture was cooled to room temperature and the pH adjusted to pH8–8.5 with dilute aqueous ammonia solution. After stirring overnight at room temperature, the product was isolated by filtration, washed with water (3×10 ml) and then dried in a vacuum oven to give the title compound as an off-white/pale brown solid (1.98 g).

Mass spectrum m/z 467 (M+1)$^+$ $^1$H NMR (d$_6$-DMSO, 400 MHz): δ 1.72 (m, 4H), 1.98 (m, 4H), 3.15 (m, 2H), 3.35 (m, 2H), 3.46 (m, 2H), 3.65 (m, 2H), 4.67 (m, 1H), 7.17 (d, 2H), 7.65 (d, 2H), 8.87 (br s, 1H), 10.58 (br s, 1H)

Similarly prepared was

Example 2

4-[4-(3-Trifluoromethylphenoxy)piperidine-1-sulfonyl methyl]tetrahydropyran-4-carboxylic Acid Hydroxyamide Prepared as Example 1 from Intermediate 7 (0.65 g) to give the title compound as a beige solid (450 mg).

TLC R$_f$0.44 (7% methanol in dichloromethane)

Mass spectrum m/z 465 (M−1)$^-$

What is claimed is:

1. A compound of formula (I):

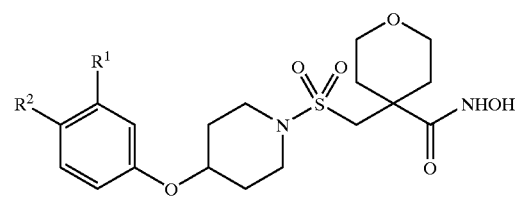

(I)

wherein:

R$^1$ and R$^2$, which may be the same or different, is each a hydrogen atom or a CF$_3$, CF$_2$H or CFH$_2$ group, provided that when one of R$^1$ or R$^2$ is a hydrogen atom the other is a CF$_3$, CF$_2$H or CFH$_2$ group; and the salts, solvates or hydrates thereof.

2. A compound according to claim 1, wherein R$^1$ is a hydrogen atom and R$^2$ is a CF$_3$, CF$_2$H or CFH$_2$ group.

3. A compound according to claim 1, wherein R$^2$ is a hydrogen atom and R$^1$ is a CF$_3$, CF$_2$H or CFH$_2$ group.

4. A compound which is 4-[4-(4-trifluoromethylphenoxy)piperidine-1-sulfonylmethyl]tetrahydropyran-4-carboxylic acid hydroxyamide; and the salts, solvates or hydrates thereof.

5. A pharmaceutical composition comprising a compound of claim 1 and a pharmaceutically acceptable diluent or carrier.

6. A compound according to claim 1 for use in the treatment of cancer, inflammation, or an autoimmune, infectious or ocular disease.

7. A compound according to claim 1 for use in the treatment of graft versus host reactions, psoriasis, atopic dermatitis, rhinitis, eczema, systemic lupus erythematosus, solid organ transplant and cystic fibrosis.

8. A compound according to claim 1, for use in the treatment of rheumatoid arthritis, osteoarthritis, osteoporosis, Crohn's Disease, ulcerative colitis, multiple sclerosis, periodontitis, bone resorption, bacterial infections, epidermolysis bullosa, tumour growth, angiogenesis, ophthalmological disease, retinopathy, asthma, emphysema, bronchitis, and chronic obstructive pulmonary disease (COPD).

* * * * *